(12) United States Patent
Yamada

(10) Patent No.: US 6,364,484 B2
(45) Date of Patent: Apr. 2, 2002

(54) OPHTHALMIC EXAMINATION APPARATUS

(75) Inventor: Takashi Yamada, Tokyo (JP)

(73) Assignee: Kowa Company Ltd. (JP)

(*) Notice: Subject to any disclaimer, the term of this patent is extended or adjusted under 35 U.S.C. 154(b) by 0 days.

(21) Appl. No.: 09/768,096

(22) Filed: Jan. 23, 2001

(30) Foreign Application Priority Data

Jul. 7, 2000 (JP) .......................................... 2000-206048

(51) Int. Cl.[7] ................................................ A61B 3/00
(52) U.S. Cl. ........................................................ 351/200
(58) Field of Search ................................. 351/200, 205, 351/206, 211, 245, 221; 250/221; 345/161

(56) References Cited

U.S. PATENT DOCUMENTS 5,252,821 A * 10/1993 Sugimura .................... 250/221

* cited by examiner

Primary Examiner—George Manuel
(74) Attorney, Agent, or Firm—Adams & Wilks

(57) ABSTRACT

An ophthalmic examination apparatus has portable ophthalmic diagnostic equipment devices each having a different ophthalmic diagnostic function. A supporting device releasably supports each of the ophthalmic diagnostic equipment devices in an operative position and permits each of the ophthalmic diagnostic equipment devices to be freely exchanged with another of the ophthalmic diagnostic equipment devices. A moving mechanism provides linear and rotational movement of the supporting device.

15 Claims, 3 Drawing Sheets

OPHTHALMIC EXAMINATION APPARATUS

BACKGROUND OF THE INVENTION

1. Field of the Invention

The present invention relates to an ophthalmic examination apparatus, and more particularly to an ophthalmic examination apparatus having ophthalmic diagnostic equipment devices that can be used as a portable or fixed system.

2. Description of the Prior Art

Ophthalmic diagnostic equipment devices known in the prior art include the fundus camera, used for diagnostic examination of the eye fundus; the slit lamp, used for diagnostic examination of the anterior portion of the eye; and the tonometer, used for measuring ocular pressure. These apparatuses are divided into fixed types used in a set location, and portable types in which part of the fixed type are omitted to enable the apparatus to be carried by hand.

There are also ophthalmic apparatuses that can be used as both fixed types and as portable types. Such types, as disclosed by Japanese Patent Laid-open Gazette Nos. 131317/97 and 234184/97, are configured as a portable type ophthalmic diagnostic system that can be detachably fitted to a fixed type system.

However, while the portable part of the system functions as a portable diagnostic system, some of the functions remain in the main fixed part of the system, so there is a high degree of linkability between the portable and fixed portions. This means that portable type ophthalmic diagnostic equipment devices having another function cannot be fitted to the fixed type. Moreover, functionally connecting the portable and fixed types requires an electrical as well as a mechanical coupling, increasing the complexity of the connection configuration.

An object of the invention is, therefore, to provide an ophthalmic examination apparatus that is structurally simple and can be readily used as a portable type or as a fixed type system.

SUMMARY OF THE INVENTION

The present invention provides an ophthalmic examination apparatus comprising, a plurality of portable ophthalmic diagnostic equipment devices having different ophthalmic diagnostic functions, means for supporting each ophthalmic diagnostic equipment device in a way that allows each device to be freely exchanged, and means for spatially moving the supporting means.

The present invention also provides an ophthalmic examination apparatus comprising, portable ophthalmic diagnostic equipment devices, means for supporting each ophthalmic diagnostic equipment device in a way that allows each device to be detachably mounted and, when a device is thus supported, effects only a mechanical coupling with the device, and means for spatially moving the supporting means.

The present invention also provides an ophthalmic examination apparatus comprising, a plurality of portable ophthalmic diagnostic equipment devices having different ophthalmic diagnostic functions, means for supporting each ophthalmic diagnostic equipment device in a way that allows each device to be freely exchanged and that, when a device is thus supported, effects only a mechanical coupling with the device, and means for spatially moving the supporting means.

DETAILED DESCRIPTION OF THE PREFERRED EMBODIMENTS

The invention will now be described with reference to the drawings.

Figure 1:
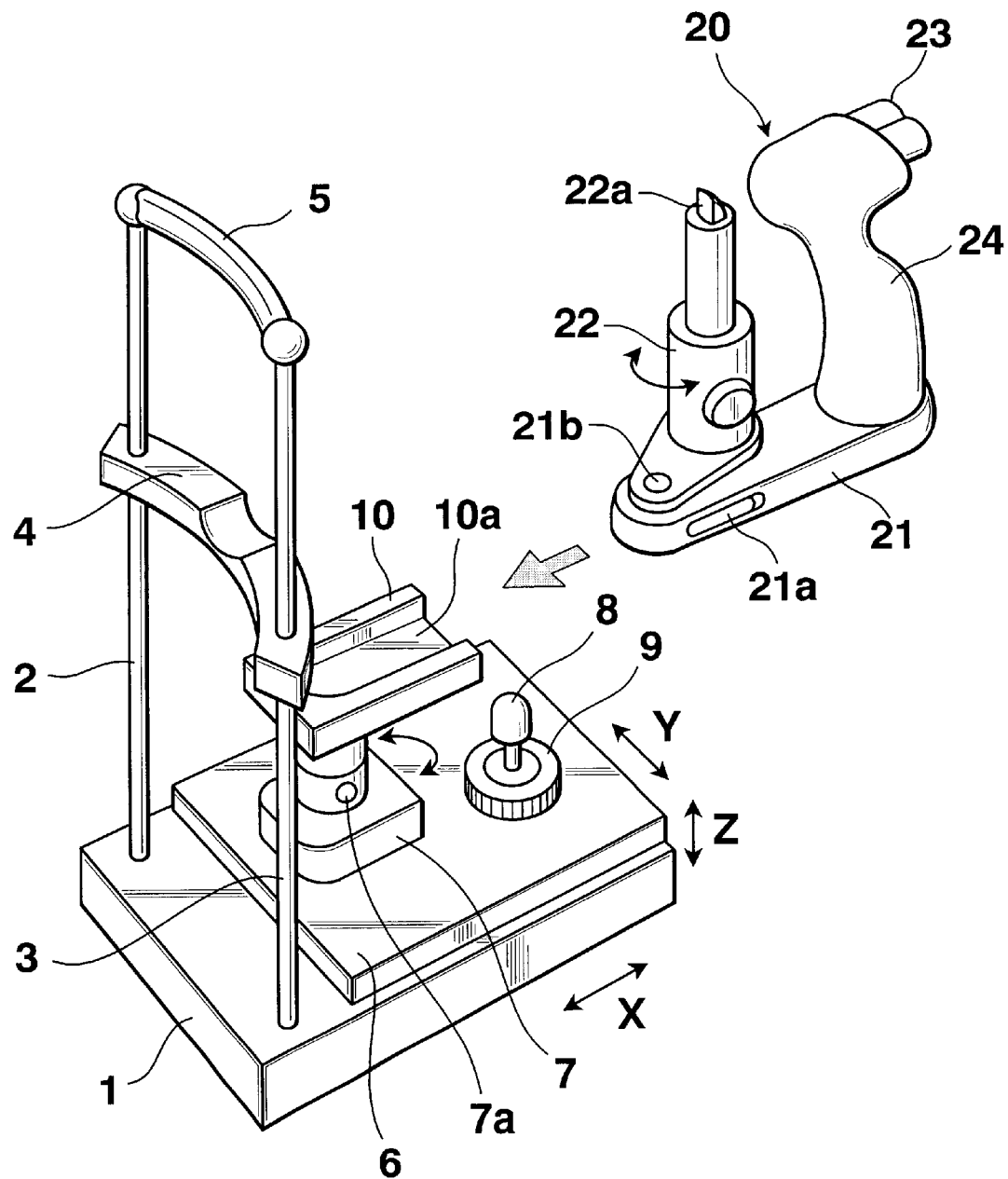
FIG. 1 is a perspective view showing the arrangement of one embodiment of an ophthalmic examination apparatus according to the present invention.
Figure 2:
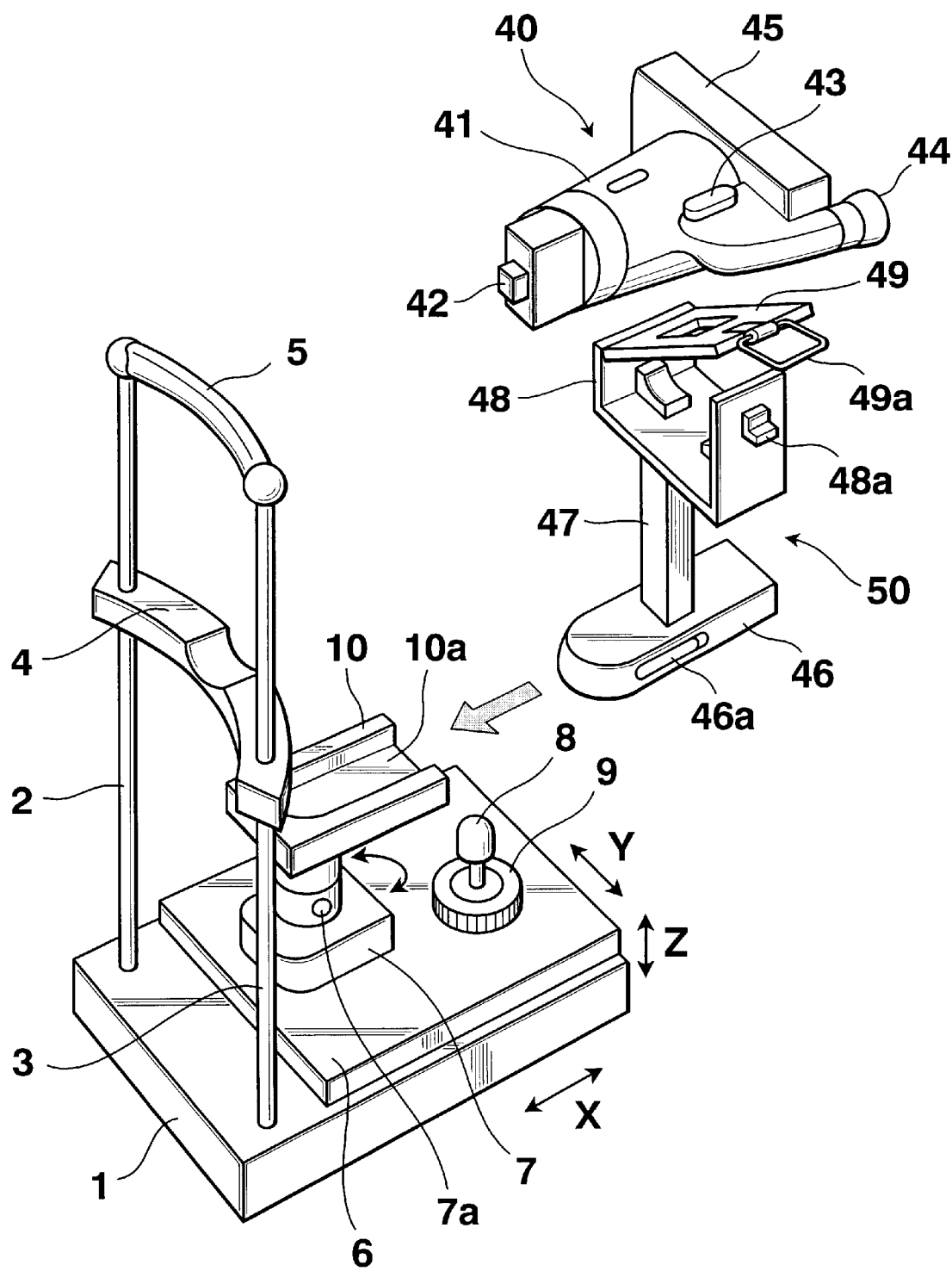
FIG. 2 is a perspective view showing the arrangement of another embodiment of an ophthalmic examination apparatus according to the present invention.

FIGS. 1 and 2 show embodiments of an ophthalmic examination apparatus according to the invention. In the drawings, reference numeral 1 denotes a base member or base of a supporting device of the ophthalmic examination apparatus, on which are fixed support uprights 2 and 3. Disposed between the uprights 2 and 3 are a chin rest 4 on which the patient being examined rests his chin, and a headrest 5 against which the patient rests his forehead. The chin rest 4 can be moved vertically to match the position of each patient's chin.

A plate member or plate 6 is mounted onto the base 1. The plate 6 is arranged so that when a lever 8 is operated, the plate 6 is moved in a horizontal plane in directions X and Y relative to the base 1, and when a ring 9 is turned, the plate 6 is moved vertically (direction Z). A block 7 is affixed to the plate 6. The block 7 supports a support base 10 in such a way that the latter can rotate about the perpendicular axis. The rotation of the support base 10 is limited by a stop-screw 7a provided on the block 7.

A U-shaped fixing recess or channel 10a is formed in the support base 10. The fixing channel 10a can be used to attach portable ophthalmic diagnostic equipment devices having various functions.

The slit lamp 20 shown in FIG. 1 is an example of a portable ophthalmic diagnostic equipment device. The slit lamp 20 has an insertion base portion or base 21 that can be inserted into the fixing channel 10a. The insertion base 21 has a pressure member 21a that is urged outwards by a spring. When the base 21 is inserted into the fixing channel 10a, the pressure member 21a is pressed inwards, allowing the slit lamp 20 to be inserted into the support base 10. When the slit lamp 20 is fully inserted, the outward spring pressure of the pressure member 21a keeps the slit lamp 20 securely attached to the support base 10. The slit lamp 20 can be removed by drawing the lamp back out, which pushes the pressure member 21a inwards, thereby enabling the slit lamp 20 to be fully removed.

A slit projection section 22 is rotatably mounted on the insertion base 21, with axis 21b as the axis of rotation. The slit lamp 20 also has a grip 24. The examiner uses the grip 24 to project the slit image onto the anterior portion of the patient's eye, via a projection window 22a, and, via eyepiece 23, observes the slit image coming from the eye.

Figure 3:
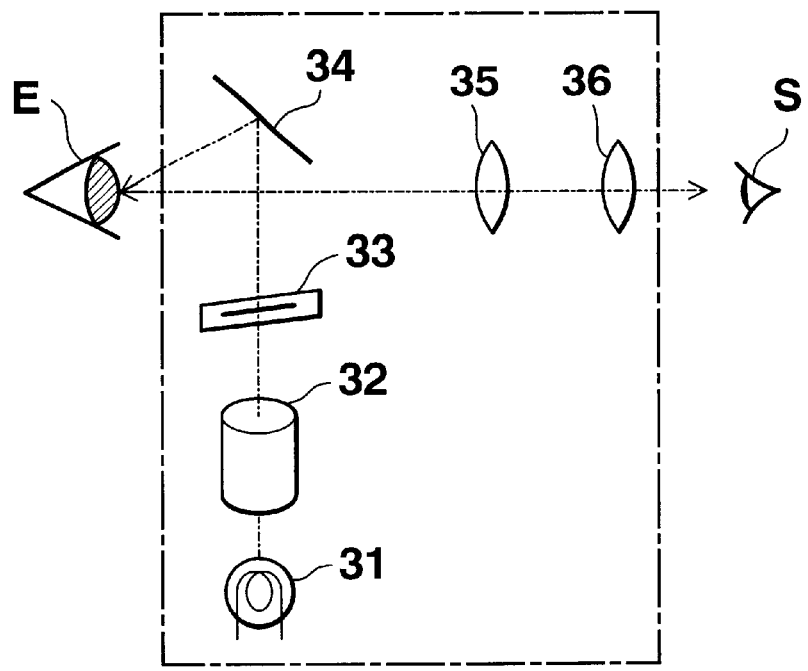
FIG. 3 is an illustrative view showing the optical system of a slit lamp.

FIG. 3 shows the optical system of the slit lamp 20. A beam of light from a lamp 31 is converted to a parallel beam by lens 32 and then passes via a slit 33 and a mirror 34 to be projected onto the anterior portion of the patient's eye E. The image of the anterior portion of the eye projected by the slit light passes via imaging lens 35 and eyepiece lens 36 for observation by the examiner S.

The slit lamp 20 itself functions as a portable type ophthalmic diagnostic device. When used for diagnostic purposes, the examiner grasps the grip 24 and switches on lamp 31 to project the slit light onto the anterior portion of the eye. Diagnosis is performed by observing the image of the reflected light through the eyepiece 23. The portability of the slit lamp 20 makes it suitable for diagnostic examinations of bedridden patients such as elderly persons as well as infants and the like. However, its very portability can be a drawback, in that it cannot be held completely still during examinations.

Therefore, when the examiner wishes to conduct a more stable, reliable examination, he inserts the insertion base 21 of the slit lamp 20 into the fixing channel 10a of the support base 10 to thereby mechanically couple the slit lamp 20 to the support base 10.

The examiner can conduct an eye examination for the patient sitting with his chin against the chin rest 4 in the same way as when the slit lamp 20 is being used as a portable system. The examiner uses the lever 8 and ring 9 to move the plate 6 horizontally and vertically to adjust the position of the slit image, and rotates the slit projection section 22 or support base 10 to adjust the direction in which the slit image is projected.

Thus, since the slit lamp 20 can detachably mounted on the support base 10 affixed to the plate 6, it can be used as a portable type device and as a fixed type. Since the slit lamp is only coupled to the support base 10 mechanically when used as a fixed type, it enables the arrangement of the fixed part to be simplified.

Other ophthalmic devices can also be used as fixed types simply by considering a mechanical coupling, i.e. by ensuring that the shape of the insertion base matches the fixing channel. FIG. 2 shows an example of this, in the form of a fundus camera 40. The camera 40 illuminates the fundus of a patient's eye and captures images of the fundus. For this, the examiner holds the body 41 of the camera and uses a switch 43 to project light through a projection window 42 to illuminate the fundus. Fundus images can be observed via an eyepiece 44, or captured using an imaging section 45 constituted by a photographic camera or CCD camera or the like.

Figure 4:
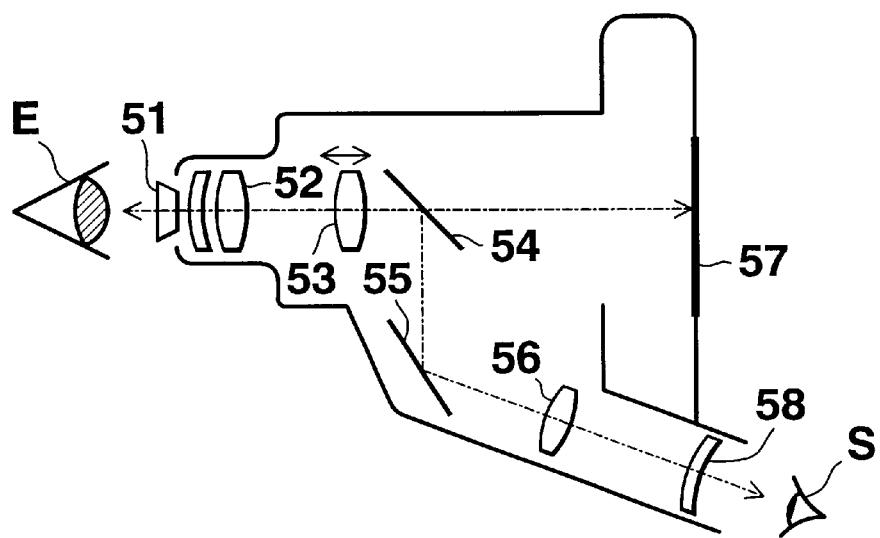
FIG. 4 is an optical view showing the optical system of a fundus camera.

FIG. 4 shows the optical system of the fundus camera 40. Illuminating light from an illumination light source and illumination optical system (not shown) is projected onto the fundus of the eye E via a prism 51. Light reflected by the fundus passes through objective lenses 52 and focusing lens 53 and falls incident on a return mirror 54. The light reflected by the return mirror 54 is then reflected by a mirror 55, and is directed to the examiner S via a field lens 56 and an eyepiece lens 58. With the return mirror 54 removed from the optical path, a flash lamp (not shown) positioned in the vicinity of the illumination light source is turned on to record images on film or another such recording medium 57.

Thus, the fundus camera 40 itself functions as a portable type ophthalmic diagnostic device, and can be used to examine the eyes of disabled patients and the like. When there is a risk that hand movement will make conditions too unstable for an examination, or when it is desired to use the camera as a fixed type system, the camera can be mounted on to the-support base 10 of the plate 6 by using an adapter 50 equipped with an insertion base 46 for insertion into the fixing channel 10a.

The insertion base 46 also has a spring-loaded pressure member 46a that enables the insertion base 46 to be detachably mounted on the-support base 10. Also affixed to the insertion base 46, via a support 47, is a fixing frame 48. To use, the examiner opens a cover 49, fits the camera 40 to the fixing frame 48, and t he n clamps the camera in place on the adaptor 50 by latching the cover hook 49a onto the lockpiece 48a. The camera is then fitted onto the fixed part of the system by sliding the insertion base 46 into the support base 10.

In this way, the examiner can use the camera 40 to examine and/or capture images of the eye in the same way as when the camera is being used as a portable system. The examiner uses the lever 8 and ring 9 to move the plate 6 horizontally and vertically to align the camera with the eye, and rotates the support base 10 to adjust the direction in which the fundus image is viewed or captured.

While this embodiment uses an adaptor 50 to fit the fundus camera 40 onto the plate 6, the camera may instead be provided with an insertion base to enable the camera to be mounted without using an adaptor.

Similarly, the electrical feed for the illumination lamp and illumination light source of the slit lamp 20 and camera 40, and the requisite power supply, can be incorporated internally or provided externally via a power cord. Even if power is provided externally, there is no need to provide an electrical connection between a device to be mounted and the fixed part of the system for receiving the device because the power does not have to be supplied via the fixed part of the system. This simplifies the system arrangement and reduces the cost.

While the aspects of the invention have been described using a slit lamp and fundus camera as examples, the invention also applies to other ophthalmic diagnostic devices, such as an ocular tonometer or other such device configured as a portable system, which can be used as a fixed system using the support base 10 on the plate 6 as shown in FIGS. 1 and 2.

As described in the foregoing, the present invention provides a simplified ophthalmic examination apparatus in which various ophthalmic diagnostic devices can be used as portable and as fixed system devices. As such, the invention can be used to build ophthalmic examination systems for a wide range of ophthalmic diagnostic applications. Moreover, when a portable device is used as a fixed system, it is only mechanically linked to the fixed part. This simplifies the arrangement of the fixed portion and also allows various ophthalmic diagnostic devices to be fitted to the fixed part.

What is claimed is:

1. An ophthalmic examination apparatus comprising:
   a plurality of portable ophthalmic diagnostic equipment devices each having a different ophthalmic diagnostic function;
   supporting means for releasably supporting each of the ophthalmic diagnostic equipment devices in an operative position to permit each of the ophthalmic diagnostic equipment devices to be freely exchanged with another of the ophthalmic diagnostic equipment devices; and
   moving means for spatially moving the supporting means.

2. An ophthalmic examination apparatus according to claim 1; wherein the moving means includes means for moving the supporting means two-dimensionally in a horizontal plane.

3. An ophthalmic examination apparatus according to claim 2; wherein the moving means includes means for rotating the supporting means about an axis perpendicular to the horizontal plane and for moving the supporting means vertically along the perpendicular axis.

4. An ophthalmic examination apparatus according to claim 1; wherein each of the ophthalmic diagnostic equipment devices has a base portion; and wherein the supporting means comprises a support base having a recess configured to receive the base portion of a selected one of the ophthalmic diagnostic equipment devices.

5. An ophthalmic examination apparatus according to claim 4; wherein the supporting means includes securing means for releasably securing the base portion of the selected ophthalmic diagnostic equipment device in the recess of the support base.

6. An ophthalmic examination apparatus according to claim 5; wherein the securing means comprises a pressure member mounted in the base portion of the selected ophthalmic diagnostic equipment device and having an engaging surface for engaging the support base when the recess of the support base receives the base portion of the selected ophthalmic diagnostic equipment device.

7. An ophthalmic examination apparatus according to claim 1; wherein the supporting means comprises an adapter member having a base portion and for removable connection to a selected one of the ophthalmic diagnostic equipment devices, and a support base having a recess configured to receive the base portion of the adapter member.

8. An ophthalmic examination apparatus according to claim 7; wherein the supporting means includes securing means for releasably securing the base portion of the adapter member in the recess of the support base.

9. An ophthalmic examination apparatus according to claim 8; wherein the securing means comprises a pressure member mounted in the base portion of the adapter member and having an engaging surface for engaging the support base when the recess of the support base receives the base portion of the adapter member.

10. An ophthalmic examination apparatus comprising: a plurality of portable ophthalmic diagnostic equipment devices each having a different ophthalmic diagnostic function and having a base portion; and a supporting device having a base member and a support base mounted on the base member for undergoing movement along a horizontal plane and along an axis disposed generally perpendicular to the horizontal plane and for undergoing rotation about the perpendicular axis, the support base having a recess configured to receive and removably secure the base portion of a selected one of the ophthalmic diagnostic equipment devices so that the selected ophthalmic diagnostic equipment device can be freely exchanged with another of the ophthalmic diagnostic equipment devices.

11. An ophthalmic examination apparatus according to claim 10; further comprising securing means for releasably securing the base portion of the selected ophthalmic diagnostic equipment device in the recess of the support base.

12. An ophthalmic examination apparatus according to claim 11; wherein the securing means comprises a pressure member mounted in the base portion of the selected ophthalmic diagnostic equipment device and having an engaging surface for engaging the support base when the recess of the support base receives the base portion of the selected ophthalmic diagnostic equipment device.

13. An ophthalmic examination apparatus comprising: a plurality of portable ophthalmic diagnostic equipment devices each having a different ophthalmic diagnostic function; an adapter member for removable connection to a selected one of the ophthalmic diagnostic equipment devices, the adapter member having a base portion; and a supporting device having a base member and a support base mounted on the base member for undergoing movement along a horizontal plane and along an axis disposed generally perpendicular to the horizontal plane and for undergoing rotation about the perpendicular axis, the support base having a recess configured to receive and removably secure the base portion of the adapter member so that the selected ophthalmic diagnostic equipment device can be freely exchanged with another of the ophthalmic diagnostic equipment devices.

14. An ophthalmic examination apparatus according to claim 13; further comprising securing means for releasably securing the base portion of the adapter member in the recess of the support base.

15. An ophthalmic examination apparatus according to claim 14; wherein the securing means comprises a pressure member mounted in the base portion of the adapter member and having an engaging surface for engaging the support base when the recess of the support base receives the base portion of the adapter member.

* * * * *